United States Patent
Samson

Patent Number: 5,926,020
Date of Patent: Jul. 20, 1999

[54] EDDY CURRENT HYBRID PROBE WITH MOVABLE MAGNETIC FIELD ALTERING MEMBER

[76] Inventor: Rock Samson, 177 de la Chaudière, Saint-Nicolas, Quebec, Canada, G0S 2Z0

[21] Appl. No.: 08/858,038

[22] Filed: May 16, 1997

Related U.S. Application Data

[63] Continuation-in-part of application No. PCT/CA95/00282, May 12, 1995.

[30] Foreign Application Priority Data

Nov. 16, 1994 [GB] United Kingdom ............... 9425146

[51] Int. Cl.$^6$ ................................ G01N 27/90
[52] U.S. Cl. .................. 324/238; 324/225; 324/232; 324/262
[58] Field of Search ..................... 324/219–221, 324/225, 232–234, 238, 240–243, 262

[56] References Cited

U.S. PATENT DOCUMENTS

| | | | |
|---|---|---|---|
| 2,124,579 | 7/1938 | Knerr et al. | 324/220 X |
| 3,611,121 | 10/1971 | Vild et al. | 324/238 |
| 3,694,740 | 9/1972 | Bergstrand | 324/238 X |
| 4,203,069 | 5/1980 | Davis | 324/220 |
| 4,608,534 | 8/1986 | Cecco et al. | 324/238 |
| 4,673,879 | 6/1987 | Harris et al. | 324/240 |
| 4,683,430 | 7/1987 | Harris et al. | 324/241 |
| 4,855,677 | 8/1989 | Clark, Jr. et al. | 324/238 |
| 5,424,640 | 6/1995 | Levy | 324/238 X |

*Primary Examiner*—Gerard Strecker
*Attorney, Agent, or Firm*—Crowell & Moring LLP; Michael D. Bednarek

[57] ABSTRACT

The eddy current probe for non-destructive testing of a conductive elongated member includes an oscillating magnetic field generator for producing a magnetic field directed towards a cross-sectional peripheral surface of the elongated member. The magnetic field generator includes a pair of coils arranged to be spaced apart along the elongated member to produce an enhanced combined magnetic field component perpendicular to the cross-sectional peripheral surface in a space between the coils and a reduced magnetic field component lengthwise along the elongated member. A ferromagnetic member is movably mounted for altering the magnetic field at points along the cross-sectional peripheral surface provided between the coils. A detecting and analyzing system measures an impedance of the coils as the generator is moved along the elongated member and as the field altering member is moved over the peripheral surface. An enhanced signal is obtained.

17 Claims, 8 Drawing Sheets

EDDY CURRENT HYBRID PROBE WITH MOVABLE MAGNETIC FIELD ALTERING MEMBER

This application is a continuation-in-part application of PCT/CA95/00282 filed May 12, 1995, in which the United States was designated and elected, and which remained pending in the international phase until May 16, 1997.

FIELD OF THE INVENTION

This invention is related to the field of non-destructive testing on tubes, pipes and rods, and more particularly to an eddy current probe and probing method for locating and measuring flaws on metallic tubes and rods.

BACKGROUND ART

The eddy current method of non-destructively evaluating metal products is widely used. Basically the method consists in moving a coil over the item to be tested. A high frequency alternating current in the coil produces an alternating magnetic field. When the magnetic field of the coil intersects the item, eddy currents are induced in the specimen close to its surface. These eddy currents in turn induce a magnetic field in opposition to the primary field around the coil, causing a partial reduction in the field of the coil. This decrease in magnetic flux through the coil causes a change in the impedance of the coil. The impedance caused by the eddy currents is in turn dependent on the resistance these currents encounter as they circulate through the item to be tested. Since flaws on the surface (such as cracks, pits, or regions of local thinning) create regions of higher resistance at the flaw locations, eddy current probes may be used to locate flaws. Eddy current testing is essentially the measurement of changes in the impedance of a probe.

In an AC bridge circuit (commonly used in eddy current testing), the change of impedance in the coil will be reflected by a change in the voltage and phase across the circuit. These changes can be analyzed and displayed with the proper equipment so that flaws can be generally characterized. To be analyzed, the AC signal is usually demodulated in its resistive and reactive components (often referred to as X and Y or real and imaginary components). The components will have similar shapes, but different amplitude depending on the AC signal phase caused by the flaw. The demodulated signals show voltage amplitude variation in time and thus allow physical localization of the flaw on the tested part.

The resistive and reactive components can be subsequently added in a vector sum. The sum is then displayed on an X-Y plane called a phasor diagram. The phasor diagram shows amplitude and phase change of the AC signal over a fixed period of time. The shape produced by flaws on the phasor diagram allows further characterization of flaws as being cracks, scorch marks, rust patches, etc.

Eddy current testing is used in many fields, such as pipe or tube inspection used in the heat exchangers of nuclear steam generators. Lately, eddy current testing has also been used for the inspection of control rods used in the core of the reactor. Usually the control rods are filled with a material which absorbs neutrons readily while the outer shell is made out of a metallic alloy such as INCONEL™. Control rods are set between fuel rods to regulate the rate of nuclear reaction. Withdrawal of the rods permits free passage of neutrons from one fuel rod to another, thus increasing the reaction rate. The control rods are guided between the fuel rods by perforated plates. Since both the control rods and the fuel rods are submersed in water—where small, constant vibrations are present—the control rods have a tendency to rub against the rim of the guiding holes in the plate thus causing damage to their surface.

In eddy current inspections, probes of the prior art generally come in one of the two following configurations: the encircling probe and the rotating probe. An encircling probe according to the prior art can be characterized by the arrangement shown in FIG. 1A which produces an output signal illustrated in FIG. 1B as the coil 20 moves over the flaw 24.

In an encircling probe (FIG. 1A), a circular coil 20 encircles the cylindrical item 22 to be inspected and moves along its length. When a flaw 24 (such as a lengthwise crack or a rusted area) is encountered, the probe registers a change in voltage across the testing circuit. The demodulated signals will simply show a voltage change over a certain period of time (FIG. 1B). The general localization and overall importance of the flaw can then be deduced.

Though mechanically simple to implement, this configuration does not allow exact flaw size measurement and localization. The response from such a probe does not permit differentiation between, for instance, four small holes and a single large one. The information obtained is the lengthwise position along the rod (or tube) where the flaw is present and relative size of the flaw. In no way can its angular position and exact size be characterized.

A rotating probe according to the prior art is generally represented in FIG. 2A which produces an output signal illustrated in FIG. 2B. In the case of rotating probes (FIG. 2A), a small energized coil 26 orbits around the cylindrical item 22 to be inspected, while traveling along its length. This results in a helical path. Since the path of the coil 26 takes it over the flaw 24 at a certain angle relative to that flaw, the probe can record its width. While the coil orbits around the tube, it passes a certain number of times over the flaw. The signal given by the probe (in terms of resistive and reactive components) resembles a series of "humps" 25 (FIG. 2B) occurring over a certain period of time. Each hump 25 is equivalent to the width of the crack surveyed by the coil. The diameter of the tube and the traveling speed of the coil being known variables, the length of the flaw and its position on the tube or rod can then be precisely determined. This kind of probe can thus determine the size, exact location and importance of the flaw.

U.S. Pat. No. 4,855,677 to Clark, Jr. et al shows a probe based on this principle but applied for use inside a tube. In this case, the rotating coil travels over the inner surface of the tube.

However, eddy current probes are often used in hostile environments (underwater, in irradiated areas of nuclear power generators). In the case of external inspections of rods and tubes, rotating probes require a complex mechanical setup for the coil to be able to orbit the rod (or tube) while still being supplied with a high frequency AC signal. Since it is highly impractical to have the AC signal source turning with the probe, slip rings are needed to feed the rotating probe with the AC signal. The friction generated by these sliding contacts creates undesired noise which affects the test results. They are also sensitive to rust and to accumulation of dirt. Probes based on that principle are subject to frequent malfunctions and early wear. This constitutes the major drawback of rotating probes.

Also, with rotating probes, it is possible that between two turns around the rod, the coil might miss a small flaw, depending on the pitch of the path of the coil around the rod.

Rotating probes also have another problem known as lift-off. During inspection, it is possible that the probe wobbles, creating a small gap between the coil an the inspected surface. This gap usually affects the accuracy of the test.

A number of patented inventions have been proposed to remedy these various problems. These prior art inventions are generally represented by the arrangement shown in FIG. 3A whose output signal is illustrated in FIG. 3B. They are based on the following principle: an encircling detector coil 28 (FIG. 3A) is mounted at axially displaced locations along the cylindrical part 22 to be inspected. To enhance the response of this detector coil, a field altering object 30 having a high magnetic permeability is mounted in close proximity to the coil. In this manner, the field altering object disrupts the coil magnetic field in continuously varying locations along the part 22 and near the coil 28 itself.

When this assembly is passed over a tube and encounters a flaw, two things will happen. When the coil 28 reaches the flaw, a first change in voltage is recorded by the analyzing circuitry. But when the field altering object 30 orbiting the coil 28 also passes over the flaw 24, an additional change of voltage is recorded. This change is a function of the volume and width of the flaw. This results in the resistive and reactive components having the appearance of two overlapping signals (FIG. 3B): one signal 27 from an encircling probe and one signal 29 from a rotating probe. One is proportional to the length of the flaw, the other characterizes its width, and both characterize its volume.

U.S. Pat. No. 4,203,069 to Davis discloses such a probe for inspecting the interior of tubes that uses this principle. The apparatus comprises an exciter/detector coil and a ferrite element mounted on the perimeter of a barrel, the barrel rotating inside the coil. The coil is energized with a high frequency signal that induces eddy currents in the tube. While this apparatus travels inside the tube, the rotating ferrite disrupts the field generated by the coil. When the probe passes over a flaw, the response is in the form of the desired two overlapping signals. The patent however does not disclose any practical method for inspecting the exterior of rods or tubes.

Another device based on the use of a coil/field altering object combination is disclosed in U.S. Pat. No. 4,673,879 to Harris et al wherein a cylindrical metallic sleeve is rotatably supported about a workpiece path of travel. Two differentially wound energization coils surround the sleeve near two apertures in the sleeve. The coils are energized with a high frequency signal that induces eddy currents in the workpiece. The apertures periodically disrupt the eddy current inducing magnetic fields and enhance signals from the coils indicative of the presence of flaws in the workpiece.

U.S. Pat. No. 4,683,430 to Harris et al also proposes a combination of an encircling coil with a field altering object. In this case two encircling coils are used, one of them comprising a tubular pathway. The pathway is positioned between the coil and the rod. A steel ball rotates inside the pathway, acting as the field altering object. However, use of a steel ball as field altering element is not very practical. Steel being highly electrically conductive by its nature, the ball will also be subject to eddy currents. These eddy currents will in turn affect the response of the probe, making it much harder to analyze.

Tests conducted by the inventor has shown that these types of combination—that is a single coil matched with a single field altering object—result in a signal that is difficult to analyze. The reason being that the strength of the signal generated by the field altering object is weak relatively to the overall signal of the encircling coil. Generally speaking, the portion of signal generated by the field altering object represents around 20% of the overall signal or even less. This makes it very difficult to determine, at the signal analysis stage, what part of the signal is generated by the field altering object. As an example, in the case of a small flaw, the signals generated by the field altering object and the encircling probe would be almost indistinguishable.

Another approach is presented in U.S. Pat. No. 3,694,740 to Bergstrand where two sets of detecting elements are used in conjunction. The first set consists in two coils that are bridge coupled or differentially coupled. A difference in potential across the circuit indicates the presence of a flaw. However, when the two coils are simultaneously placed over a long flaw, the circuit will respond as if no flaw was present. To compensate for this, a second set consisting of a pair of Hall effect elements—connected to a differential amplifier—orbits the inspected part near the coils. A positive or negative output of the amplifier indicates the presence of a flaw. This type of probe possesses two major drawbacks. First, if the flaw is two dimensional (which would be the case of a long patch of rust), there is a strong possibility that both Hall effect elements would be over the flaw simultaneously. The differential amplifier would then also respond as if there were no flaw. As a result, the rust patch would go undetected. The second drawback resides in the necessity of slip rings and brushes to feed power and remove the signal from the rotating elements. This makes this type of probe just as prone to early wear and breakage as the rotating probe described above and disclosed by Clark.

OBJECTS OF THE INVENTION

To remedy these drawbacks, the invention has several objects.

The first object of the invention is to provide an hybrid eddy current probe that eliminates the need for a slip ring, while still retaining the flaw measuring capabilities of the rotating probe.

The second object is to provide a probe that is mechanically simple and dependable.

The third object is to provide an hybrid eddy current probe that can characterize flaw size, position and importance without the risk of missing a smaller flaw.

The fourth object is to provide an hybrid eddy current probe in which the signal of the field altering object represents around 50% of the overall response of the probe to a flaw. That augmentation in signal ratio facilitates distinction between the portions of signal generated by the encircling coil and the field altering object.

The fifth object is to provide a probe in which the probe response to a flaw is composed only of the signal generated by the field altering object. The resulting signal would be identical to the signal produced by a rotating probe.

Another object of the invention is to provide rod testing apparatus capable of testing several rods at the same time.

A further object is to provide a probe based on the principle of the invention for use in internal inspection of tubes.

SUMMARY OF THE INVENTION

The present invention provides a method and an apparatus of the general type known in U.S. Pat. No. 4,673,879. According to the invention, there is provided an eddy current probe for non-destructive testing of a conductive elongated member in which the probe comprises means for generating an oscillating magnetic field directed towards a cross-sectional peripheral surface of the elongated member including a pair of coils arranged to be spaced apart along the elongated member to produce an enhanced combined magnetic field component perpendicular to the cross-sectional peripheral surface in a space between the coils and a reduced magnetic field component lengthwise along the elongated member, movable or rotatable means for altering the magnetic field at points along the cross-sectional peripheral surface provided between the coils, and means for detecting and analyzing an impedance of the generating means as the generating means is moved along the elongated member and as the rotatable altering means is moved over the peripheral surface.

According to the invention, there is also provided a method for non-destructive, eddy current testing of a conductive elongated member comprising the steps of generating an oscillating magnetic field directed towards a cross-sectional peripheral surface of the elongated member using a pair of coils arranged to be spaced apart along the elongated member to produce an enhanced combined magnetic field component perpendicular to the cross-sectional peripheral surface in a space between the coils and a reduced magnetic field component along the elongated member, altering the magnetic field at points around the peripheral surface between the coils, and detecting and analyzing a permeability of the elongated member along the elongated member and at points along the peripheral surface.

BRIEF DESCRIPTION OF THE DRAWINGS

The invention will be better understood by way of the following detailed description of a preferred embodiment, with reference to the appended drawings, in which.

DETAILED DESCRIPTION OF THE PREFERRED EMBODIMENT

Figure 3A:
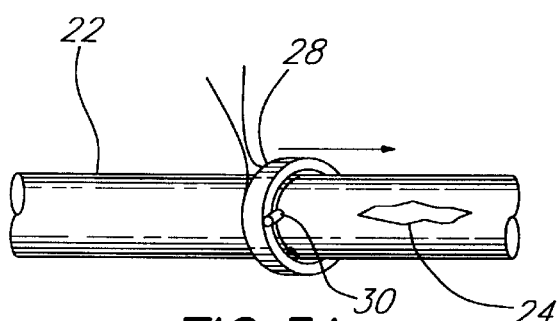
FIG. 3A is a schematic view of an encircling probe combined with a field altering object of the prior art.
Figure 3B:
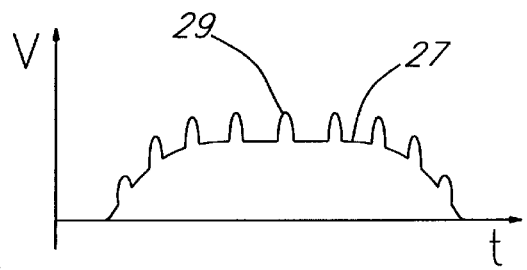
FIG. 3B is a voltage/time graph of the response of an encircling probe combined with a field altering object of the prior art.
Figure 4:
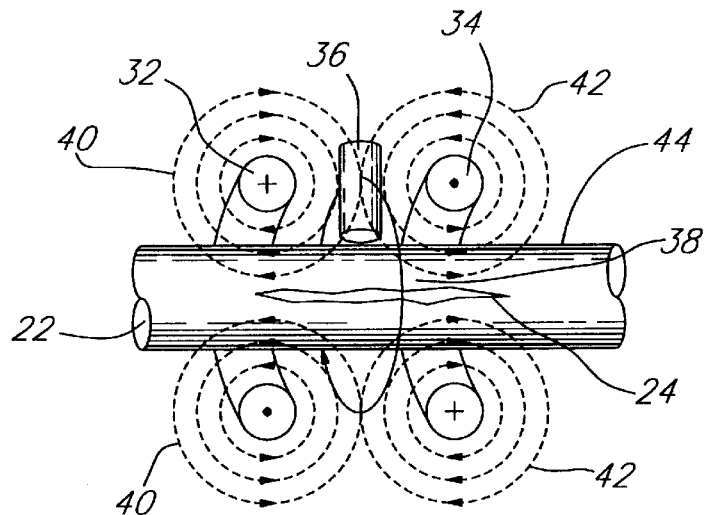
FIG. 4 is a schematic view of the hybrid probe of the preferred embodiment used over a rod.

As mentioned before, in the prior art the effect of the probe is field altering object generally represents about 20% of the total strength of the probe response to a flaw (FIG. 3B). To push this percentage past the 50% mark, in the preferred embodiment, the configuration illustrated in FIG. 4 is used. Instead of using a single coil, two coils 32 and 34 are used, side by side and in relatively close proximity, with a field altering object 36 rotating in the space between the coils. Preferably the field altering object 36 has a very high magnetic permeability and the lowest possible electrical conductivity. The two coils 32 and 34 are energized with the same high frequency signal but are wired so that the current flows in opposite directions in each coil. This has a direct effect over the combination of the magnetic field 40 and 42 generated by the coils. In the space between the coils—that is along the path 38 of the field altering object—the magnetic fields flow in the same direction, thus being added together. Over the surface 44 of the inspected object 22, the fields flow in opposite directions, thus subtracting themselves. As a result, the part of the response signal affected by the field altering object 36 is strengthened while the effect of the coils 32 and 34 over the surface is diminished. The inventor has observed that this configuration allows the portion of the signal affected by the field altering object to amount to about 50% or even 70% of the overall response of the probe to a flaw 24. The demodulated resistive and reactive component signals will look like FIG. 6.

While distance between the encircling coils 32 and 34 an the surface 44 may vary according to the conditions of the inspection, it is important that the field altering object 36 be as near as possible to the surface 44. It is also important that one extremity of the object 36 be between the two coils at all times. In the preferred embodiment, the field altering object 36 is cylindrical and orbits between coils 32 and 34 so that it is always perpendicular to the surface 44 of the cylindrical part 22. The coils 32 and 34 should be as near as possible to the object 36 without interfering with its movement.

Figure 5:
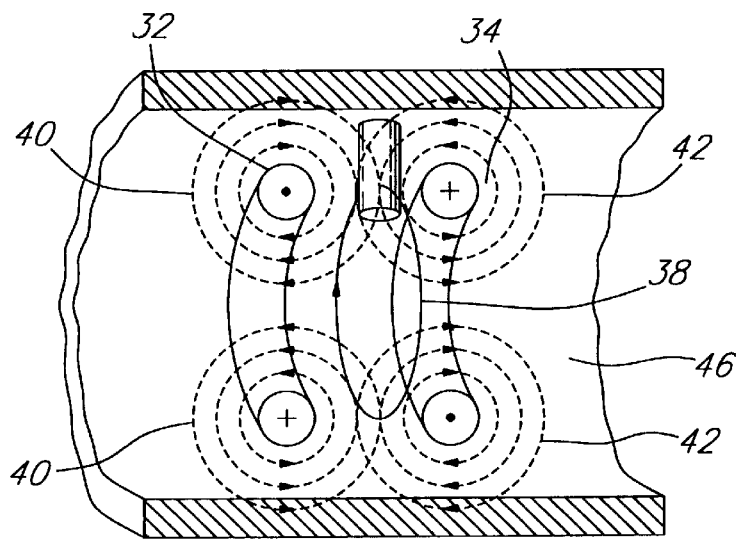
FIG. 5 is a schematic view of the hybrid probe of the preferred embodiment used inside a tube.

As shown in FIG. 5, this arrangement can also be adapted for use inside tubes. A pair of coils 32 and 34 and a field altering object 36 are still used. In this case however, the current flow within the coils is reversed, so that the magnetic fluxes 40 and 42 from each coil still subtract themselves from each other over the interior wall 46 of the tube. However, the fluxes still add up along the path 38 of the coil. The response to of this arrangement to a flaw would also look like FIG. 6.

Figure 7:
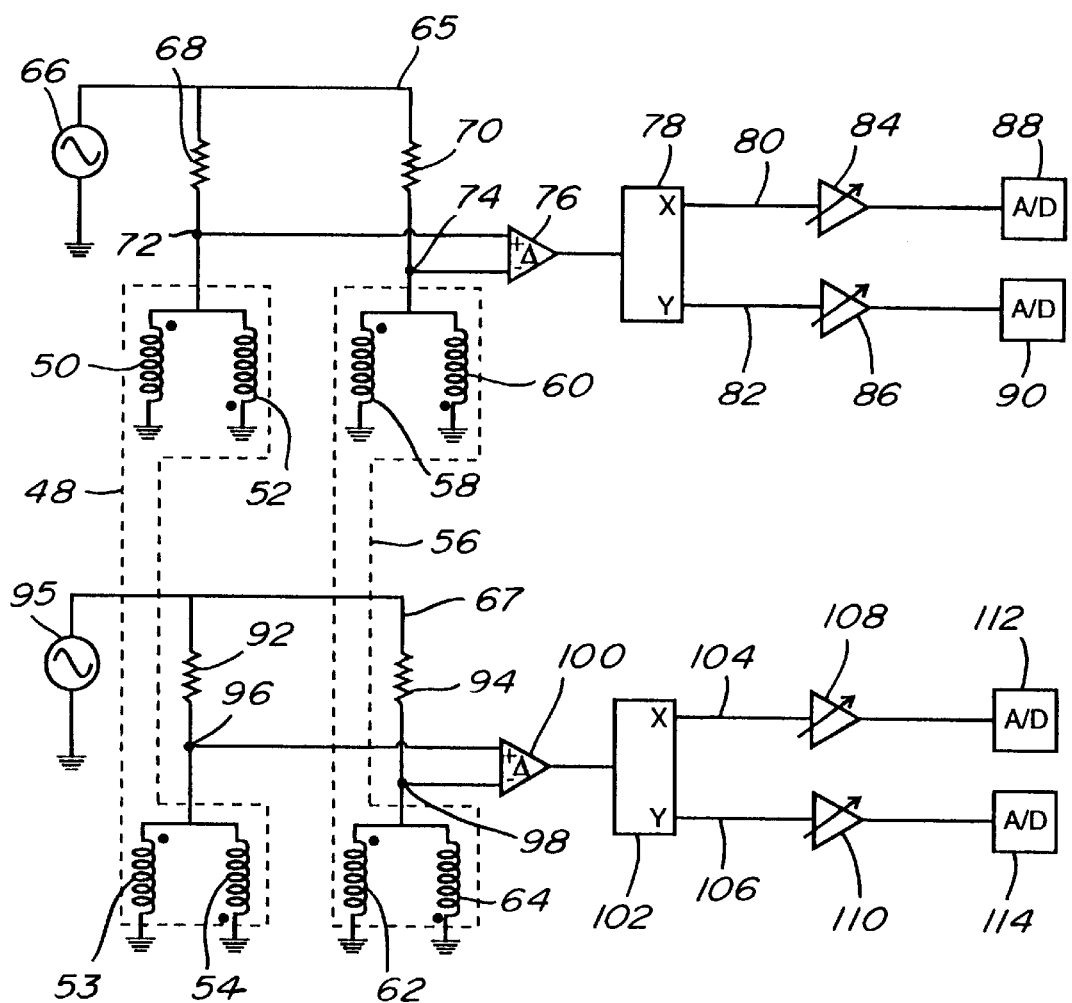
FIG. 7 is an electrical schematic of a bridge circuit using the preferred embodiment of the invention.

Most eddy current instrumentation use an AC bridge to sense the slight change in impedance between the detection coils and a reference impedance. The preferred embodiment—that can be used to test control rods in nuclear reactor—of the present invention is illustrated in FIG. 7, where one can see a diagram of the basic excitation/detection circuitry. In this embodiment, a typical hybrid probe 48 features a total of four encircling coils divided in two pairs. A first pair comprises detection coils 50 and 52 between which the field altering object turns, and a second pair comprises correction coils 53 and 54. Detection coils 50 and 52 and correction coils 53 and 54 are separated by the necessary distance so that their magnetic fields do not influence each other. Coils 50, 52 and the field altering object are arranged according to the configuration illustrated in FIG. 4. Correction coils 53 and 54 are identically arranged with the exception that no field altering object is present. The signal coming from the pair of correction coils 53 and 54 is later subtracted from the signal of detection coils 50 and 52. When the probe passes over a flaw, the response signal of the hybrid probe will be similar to that of the rotating probe.

Impedance changes in the probe are not only generated by the flaws, but can also by affected by other factors, such as ambient temperature. Also a reference signal is needed to insure balance in the bridge circuit. The reference signal is taken from another identical probe (called a reference probe 56) where a flawless section of rod is inserted. The signal from the reference probe 56 is subtracted (in an AC bridge) from the signal generated by the inspecting probe 48. The resulting response is as much as possible only influenced by the presence of a flaw. The reference probe 56 comprises its own pair of detection coils 58 and 60 and its pair control of coils 62 and 64. A field altering object is also placed between coils 58 and 60. However, in the reference probe, it is not necessary that the object be in motion. If an array of rods is used with a corresponding array of probes, only one reference probe can be used for all the probes of the array. It is important that the reference 56 probe be located in the same environment as probe 48, which actually performs the test. Otherwise the impedance changes due to the environment will to be compensated.

In all probes, each pair of coils is connected in parallel but the coils are wound in opposite directions, according to the configuration illustrated in FIG. 7.

To perform the tests, the coils from the two probes 48 and 56 (FIG. 7) are wired together to form two AC bridge circuits. In the first bridge circuit 65, the first arm is composed of the pair formed by coils 50 and 52 (that are enhanced by a field altering object) of testing probe 48. The second arm is composed of coils 58 and 60 of the reference probe. The third and forth arms comprise resistive elements 68 and 70. Physically the resistive elements 68 and 70 are often part of an AC signal driver comprising the AC current source 66 of the bridge. Points 72 and 74 are connected to a differential amplifier 76. Point 72 is connected to the positive input of amplifier 76 while point 74 is connected to the negative input.

Resistive elements 68 and 70 are chosen so that when probe 48 passes over a flawless area, the bridge is in balance. Balance is indicated by a zero response from the differential amplifier 76, which means that points 72 and 74 have the same instantaneous voltage. Since both probe 48 and reference probe 56 share the same environment, any impedance change due to temperature will be compensated/canceled in the differential amplifier.

The AC signal from the amplifier is then fed into an analyzer or demodulator 78 to be separated into its resistive 80 and reactive 82 components. At this point, the resistive and reactive components of the AC signal—when encountering a flaw—can be illustrated as in FIG. 6. Demodulated signals 80 and 82 can then be amplified by variable gain amplifiers 84 and 86 before being converted to digital signals by analog-to-digital converters 88 and 90. The digital signal can later be processed by analyzing software. The differential amplifier 76, demodulator 78, variable gain amplifiers 84 and 86 and analog-to-digital converters 88 and 90 are all components of the signal acquisition hardware to which the probe output is fed. Such signal acquisition hardware can be readily supplied by manufacturers of eddy current testing equipment.

The second bridge 67 has the same layout as the first. In this case however, the first arm is composed of the pair formed by coils 53 and 54 of testing probe 48, the second arm is composed of coils 62 and 64 of the reference probe 56, the third and forth arms comprise resistive elements 92 and 94. Physically the resistive elements are often part of an AC signal driver comprising AC current source 95. Point 96 and 98 are connected to a differential amplifier 100. Point 96 is connected to the positive input of amplifier 100 while point 98 is connected to the negative input.

Resistive elements 92 and 94 are chosen so that when probe 48 passes over a flawless area, the second bridge 67 is in balance. Balance is indicated by a zero response from the differential amplifier 100. Since both probe 48 and reference probe 56 share the same environment, any impedance change due to temperature will be nulled in the differential amplifier.

The AC signal from the amplifier is then fed into a demodulator 102 to be separated into its resistive 104 and reactive 106 components. At this point, the component of the AC signal—when encountering flaw—will look like FIG. 2B. Demodulated signals 104 and 106 can then be amplified by variable gain amplifiers 108 and 110 before being converted to digital signals by analog-to-digital converters 112 and 114. The digital signal can later be processed by analyzing software. The differential amplifier 100, demodulator 102, variable gain amplifiers 108 and 110 and analog-to-digital converters 112 and 114 are also components of the same signal acquisition hardware that is used in the first bridge.

The analysis part is often performed on a tabletop computer which is equipped with the hardware necessary for the computer to accept the digital signals. Now the analysis software can use two signals: one coming from the first bridge 65 (which is a signal affected by a field altering object) and one coming from the second bridge 67.

Figure 6:
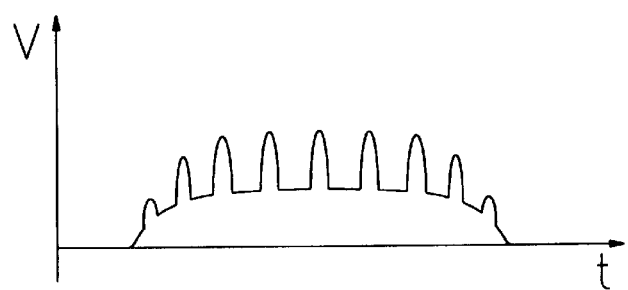
FIG. 6 is a voltage/time graph of the response of the hybrid probe of the preferred embodiment.

As described above, the demodulated signals 80 and 82 coming from the first bridge have the shape illustrated in FIG. 6. Any of the two signals can be directly used to characterize the width, length and volume of the flaw. Any small flaw that might be missed by the field altering object will show in the portion of the signal generated by the encircling coils.

However, since it disturbs the magnetic field, the rotating field altering object generates a small "parasite" signal even when the probe passes over a flawless part of a rod. This can be filtered out by the data analysis software. The filtering process is simple. A series of digital "prints" of the signal of the probe passing over a flawless rods is first recorded with the eddy current hardware. An average of these signals is calculated. The resulting signal is then subtracted from the signal given by the probe. This subtraction is digitally performed by the data analysis software.

Figure 1A:
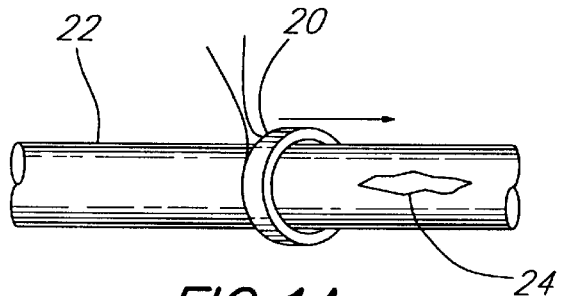
FIG. 1A is a schematic view of an encircling probe of the prior art.
Figure 1B:
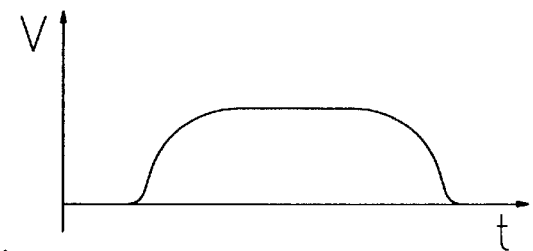
FIG. 1B is a voltage/time graph of an encircling probe's response to a flaw of the prior art.
Figure 2A:
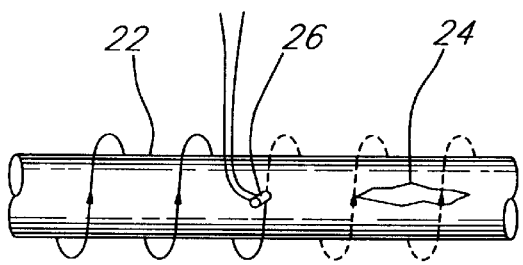
FIG. 2A is a schematic view of a rotating probe of the prior art.
Figure 2B:
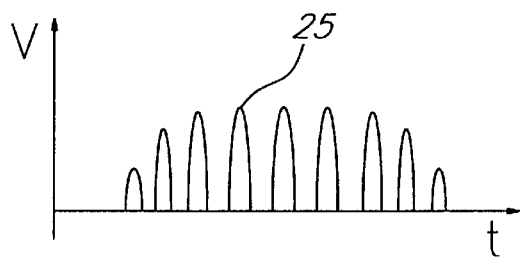
FIG. 2B is a voltage/time graph of a rotating probe's response to a flaw of the prior art.

It is often useful to obtain resistive and reactive components signals similar to the output given by a rotating probe (FIG. 2B). This is when the signals from second bridge 67 come into play. The signals from the second bridge 67 fed to the data analysis software are those of encircling probes (FIG. 1B). If they are subtracted from the signals from the first bridge 65 (FIG. 6) the resulting output will be similar to that of a rotating probe (FIG. 2B). Once again this subtraction is performed digitally by the analyzing software. Of course the software takes into account the delay between the signals from the first bridge and the signals from the second bridge.

The final result consists of two demodulated signals: the resistive and reactive components. These can be analyzed and viewed in any fashion desired and also displayed in a phasor diagram.

Figure 10:
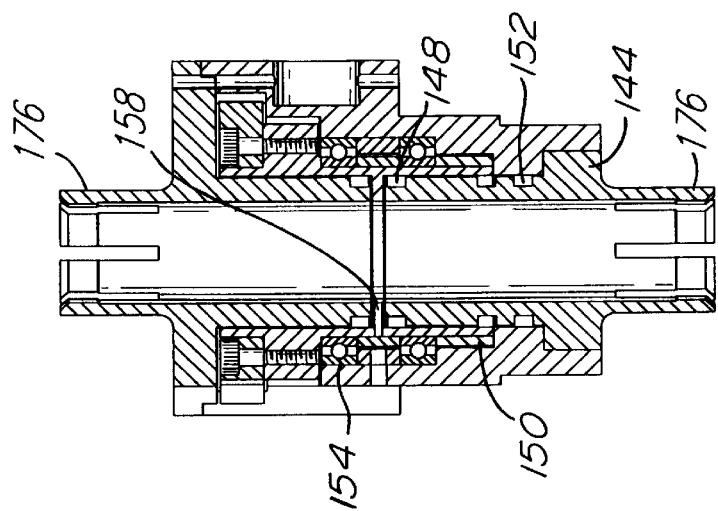
FIG. 10 is a cross-section according to line 10—10 of FIG. 9.
Figure 9:
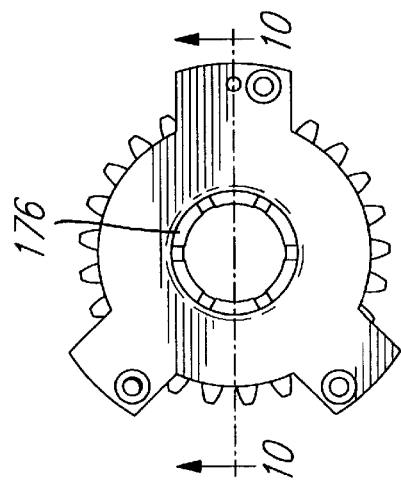
FIG. 9 is a top view of the probe of FIG. 8.
Figure 8:
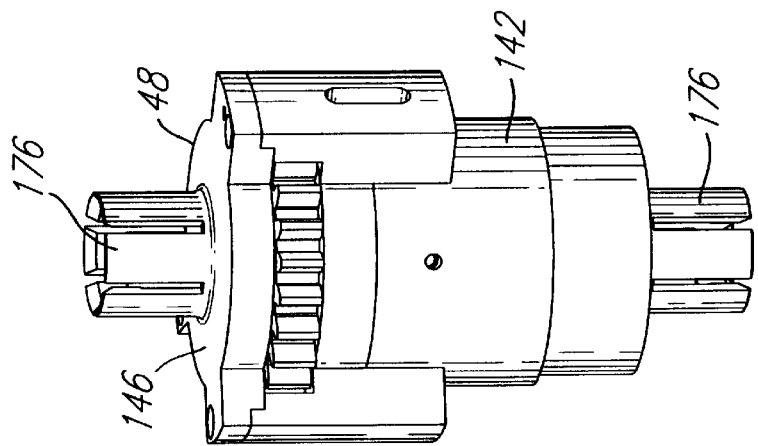
FIG. 8 is an isometric view of the probe of the invention for inspection of rods.
Figure 11:
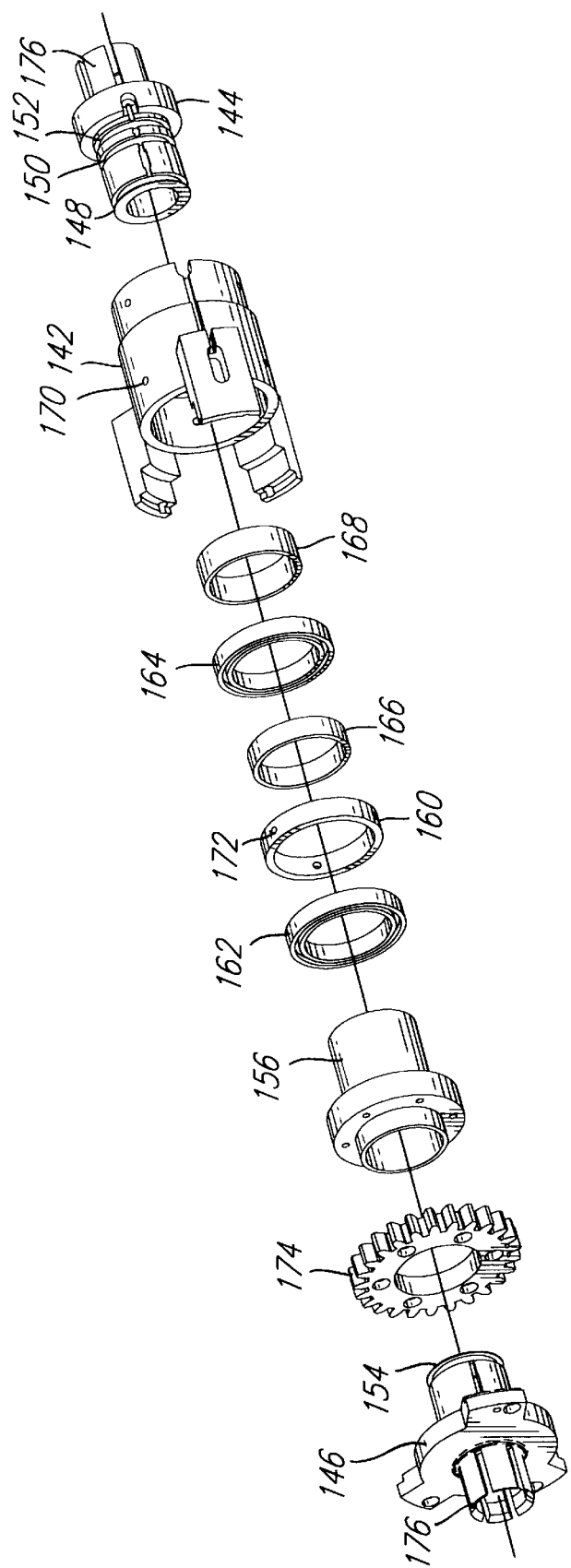
FIG. 11 is a exploded view of the probe of FIG. 8.

The hybrid probe according to the preferred embodiment of the invention is quite straightforward. An embodiment is shown in FIGS. 8, 9 and 10 where one can see a complete probe 48 comprising a hollow main body 142, a triple coil support 144 inserted at the bottom of the main body and single coil support 146 that also serves to close the top of the main body. The triple coil support 144 (FIG. 11) comprises three grooves 148, 150 and 152, each receiving a coil. Single coil support 146 receives a single coil in groove 154. Both single coil support 146 and triple coil support 144 are hollow to permit passage of the rod or tube to be inspected.

In the excitation/detection circuitry of the preferred embodiment, groove 154 receives coil 50. Grooves 148, 150 and 152 would respectively receive coils 52, 58 and 60. The field altering object orbiting between coils 50 and 52 is supported by a rotating sleeve 156. The field altering object used is a small ferrite. Ferrite possesses the great advantage of having a high magnetic permeability combined with a low electrical conductivity. The ferrite is inserted in the periphery of rotating sleeve 156, in a positioning hole 158 (FIG. 10).

The rotating sleeve 156 (FIG. 11) is supported inside main body 142 by an external ring 160, a first ball bearing 162 and a second ball bearing 164. A first spacer ring 166 is inserted immediately after bearing 162 to keep it in place. The outside diameter of spacer ring 166 is smaller than the inside diameter of the external ring 160, allowing for free rotation of external ring 160. Bearing 164 is maintained in place (against spacer ring 166) by a second spacer ring 168. Rotating sleeve 142 is secured to the interior of the main body 156 by screws, using holes 170 on main body 142 and holes 172 on external ring 160. Centering fingers 176 are peripherally mounted on the top single coil support 146 (where the rod enters) and on the bottom triple coil support 144 (where the rod exits). The centering fingers 176 are use to precisely center the probe around the rod. The fingers also eliminate any wobbling of the probe, which might cause an effect similar to the lift-off of rotating probes.

Figure 12:
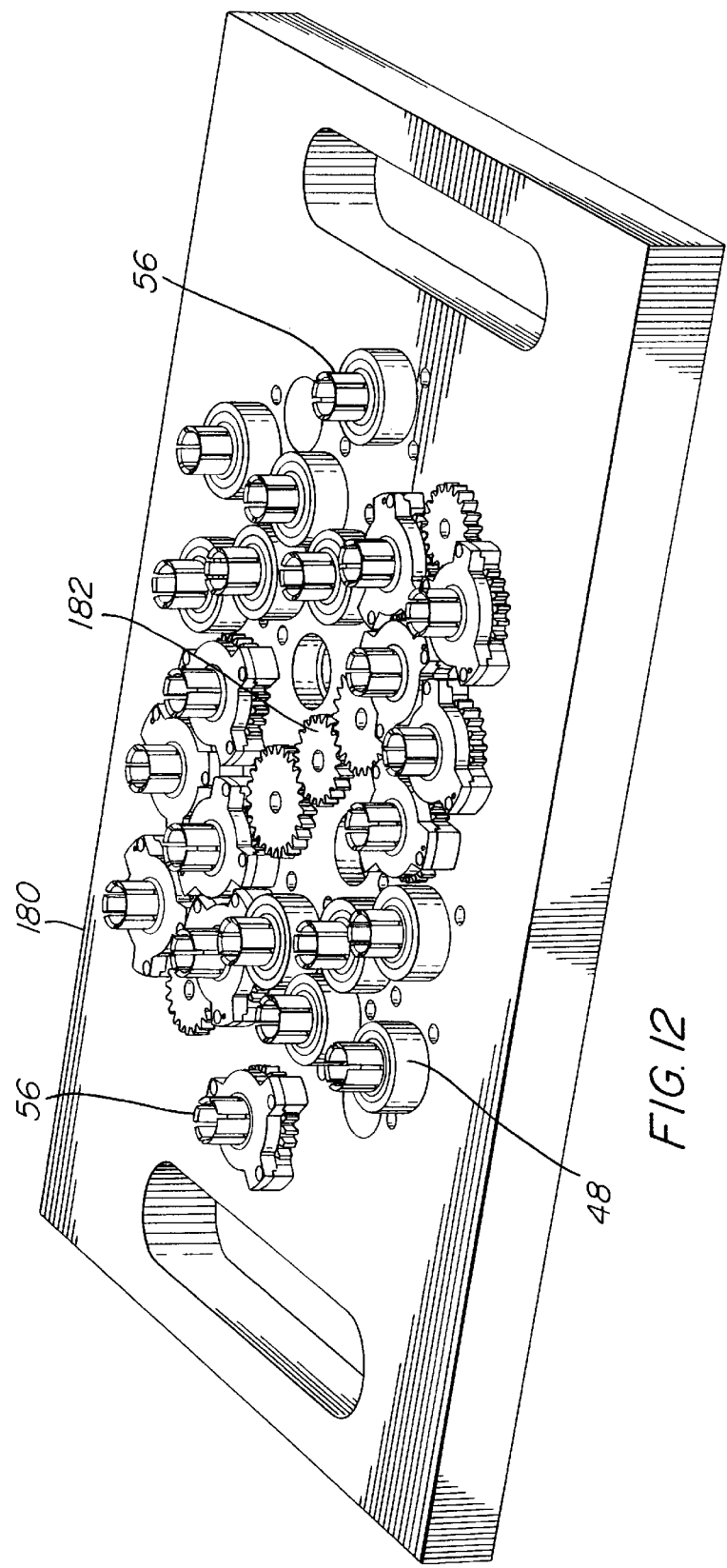
FIG. 12 is a cross-section along line 12—12 of FIG. 11.

Rotation is transmitted to rotating sleeve 156 via a gear 174 attached on top of the rotating sleeve 156. In this arrangement, multiple probes can be mounted vertically on a table 180 (FIG. 12) and movement to the ferrite of all the probes can be provided by a single motor via a series of gears 182 or by installing the probes close enough so that their individual gears 174 come in contact. Rotation can then be transmitted directly from one gear to another. Reference probes can also be mounted on the table 180. As described above, they do not need rotation of the field altering element. Flawless piece of rod are then simply inserted in the reference probe. During the inspection, the rods are lowered together through the probes at a constant speed. This eliminates the need to actually move the probe along the rod since the relative movement is the same.

When the probe is assembled, the ferrite rotates between the coils in grooves 154 and 148 (FIG. 10). This reproduces the arrangement of FIG. 4. If only one coil were used, the additional signal generated by the passage of the ferrite 158 would be relatively small (about five to six times smaller) compared to the signal of the encircling coil in groove 154. Sandwiching (without any actual contact) the rotating ferrite between coils with opposing magnetic fields, allows the ratio of the two signals to be closer to 1:1 or even 2:1. Coils in groove 154 and 148 are those used in the first bridge of the circuit illustrated in FIG. 7.

With the exception of bearings 162 and 164, gear 174, ferrite 158 and the coils themselves, all components are made out of polyetheretherketone (also known as Polyenko® PEEK) a light plastic. Polyetherethereketone is a material that features excellent flame retardance and high heat resistance. But most importantly the material is resistant to gamma radiation, which is very important for use in nuclear power plants. Use of this material makes the probe very light and easy to manufacture.

The probe according to the invention could alternatively be adapted to inspect the inside of tubes. In this embodiment, the both the ferrite and the encircling coils would travel inside the tube. The working principle remains the same with the exception that the surface to be inspected surrounds the encircling coil/orbiting ferrite combination as seen in FIG. 5. The probe thus comprises an internal rotating mechanism to allow the coils and the ferrite to be near the interior wall of the tube. Movement of the ferrite is provided by a small motor inside the probe.

Figure 13:
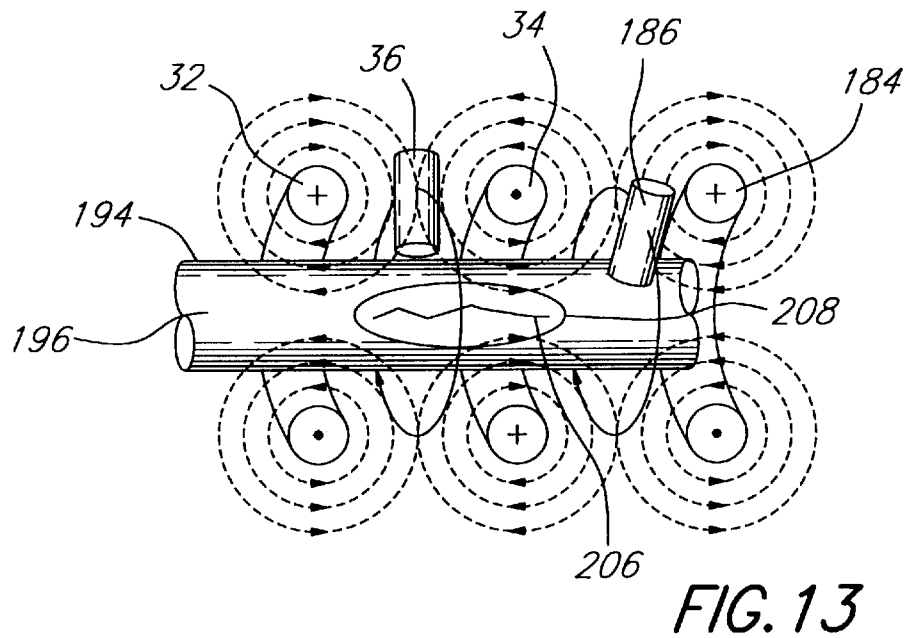
FIG. 13 is schematic view of the hybrid probe of the alternative embodiment having three coils used over a rod.

In some applications, the item to be inspected might feature random localized changes in magnetic properties. These changes may not be due to flaws, but might result from normal variation in the production process, localized change in temperature or some other phenomenon. These changes however are picked up by the probe and might render difficult the characterization of real flaws (such as narrow cracks or pitting). It might then be interesting to further augment the resolution of the probe. The object is to discriminate between random localized changes in magnetic properties and flaws which could be concealed in them. To do this, the arrangement according to the alternative embodiment shown in FIG.13 may be used. This arrangement shares the basic design of the preferred embodiment, namely: a pair of coils 32 and 34 between which rotates a field altering element 36. A second pair is formed by coils 34 and 184 between which rotates a second field altering element 186.

Figure 16:
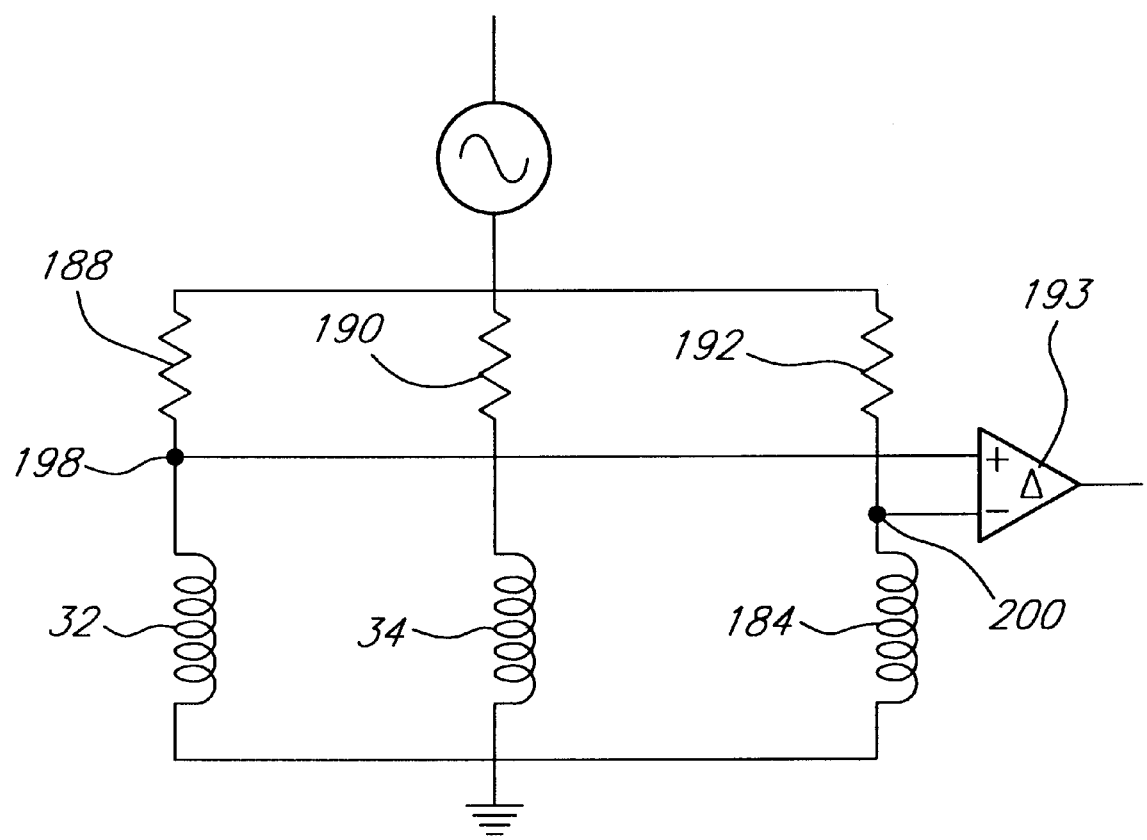
FIG. 16 is an electrical schematic of a bridge circuit using the alternative embodiment of the invention.

These components are wired to form the bridge shown in FIG. 16. The resistive elements 188, 190 and 192 are chosen so that when the probe passes over a flawless area, the bridge is in balance. Balance is indicated by a zero response from differential amplifier 193. The three coils 32, 34 and 184 (FIG.13) are energized with the same high frequency signal but are wired so that the current flows in opposite directions in each coil. Again, in the space between the coils, i.e. along the paths of the field altering object 36 and 186, the magnetic fields flow in the same direction, thus being added together. Over the surface 194 of the inspected object 196, the fields flow in opposite directions, thus subtracting themselves. As a result, the part of the response signal affected by the field altering objects 36 and 186 is strengthened while the effect of the coils 32, 34 and 184 over the surface is diminished. This generates, for both pair of coils, the same improvement in probe response as the original embodiment. Note that the second field altering element rotates in at an angular position slightly offset from the first field altering element 36. In this arrangement, only the outer coils 32 and 184 are used for measurements. The center coil is simply there to enhance the magnetic field. To that purpose, the value of resistive element 190 is usually halved relatively to the value of resistive elements 188 and 192. Thus, the current is augmented in coil 34 and the resulting magnetic field is sufficient to keep the field enhancing effect equivalent to that of the original embodiment in both pair of coils.

Figure 14:
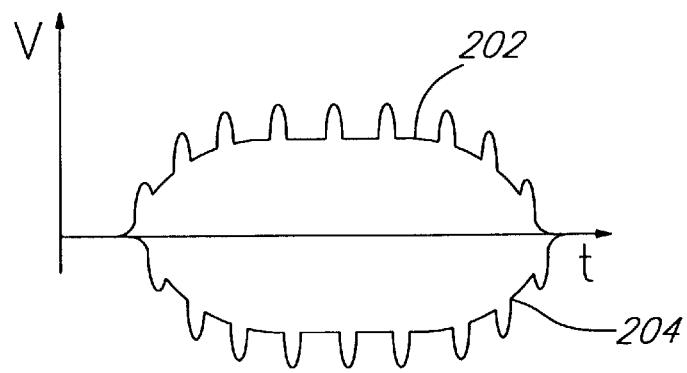
FIG. 14 is a voltage/time graph of the response of the end coils of the alternative embodiment.
Figure 15:
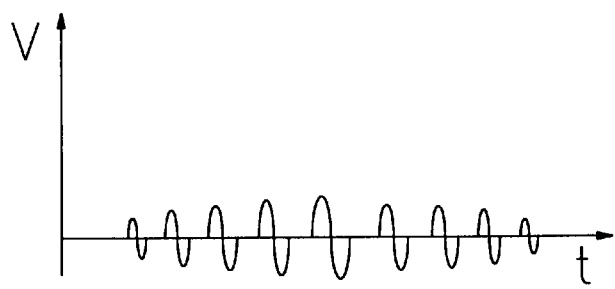
FIG. 15 is a voltage/time graph of the difference of the response of the end coils of the alternative embodiment.

When the probe passes over a localized change in magnetic properties 206 in which is located, for example, a thin lengthwise crack 208, the demodulated resistive and reactive component signals will look like FIG. 14. The signal measured at point 198 (see FIG.16) will look like curve 202. The signal measured at point 200 will look like curve 204. Curve 204 is shown negative for clarity. In both curves, the large bell shape is generated by the large flaw. The smaller crack is revealed by the little peaks on top of the bells. When the two signals are combined in the differential amplifier 193, the large bell shapes cancel each other out. But since the second field altering element 186 passes over the flaw before field altering element 36, its signal precedes that of field altering element 36. As a result, the peaks from positive curve 202 and negative curve 204 do not cancel each other out. The result looks like the curve on FIG. 15. One can see that the signal generated by the narrow lengthwise crack is the only one remaining. It is thus much more easier isolate and analyze.

In another embodiment, the field altering element could be replaced by a rotating coil from which measures are taken. The probe is then similar to a rotating probe except that the pair(s) of coils are used in a field enhancing function instead of a flaw detecting one. It will be appreciated that this arrangement can be applied to all the preceding embodiments.

Although the invention has been described in detail with reference primarily to the preferred embodiment, this should not be construed as limiting the scope of the invention as defined in the appended claims.

What is claimed is:

1. An eddy current probe for non-destructive testing of a conductive elongated member, said probe comprising means for generating an oscillating magnetic field directed towards a cross-sectional peripheral surface of said member, said generating means including a pair of coils arranged to be spaced apart along said member to produce an enhanced combined magnetic field component perpendicular to said surface in a space between said coils and a reduced magnetic field component along said member, movable means for altering said magnetic field within a small area to be observed, said movable means being mobile to move said area along said cross-sectional peripheral surface between said coils to cover points along said peripheral surface, said movable means being provided substantially mid-way between said coils.

2. The probe as defined in claim 1, wherein said movable means comprise a ferromagnetic member for altering said magnetic field within said small area to be observed covering said points along said peripheral surface.

3. The probe as defined in claim 1, wherein said movable means are rotatable, said elongated member being of circular cross-section.

4. The probe as defined in claim 1, further comprising separate reference probe means having a structure and function similar to said probe for testing a reference conductive elongated member, and means for subtracting an impedance signal Generated by the reference probe means from an impedance signal generated by said probe.

5. The probe as defined in claim 1, wherein said probe is arranged to surround said elongated member, said oscillating magnetic field being directed inwardly towards said cross-sectional peripheral surface.

6. The probe as defined in claim 1, wherein said probe is arranged to be within said conductive elongated member, said magnetic field being directed outwardly towards a cross-sectional peripheral surface of said elongated member.

7. The probe as defined in claim 1, further comprising correction probe means connected to said probe at a non-interfering distance from said generating means and including a pair of coils arranged substantially identically to said coils of said generating means, said correction probe means having a space between its pair of coils free from any magnetic field altering means, and means for subtracting an impedance signal generated by the correction probe means from an impedance signal generated from said probe.

8. The probe as defined in claims 3, wherein said movable means comprise a ferromagnetic member for altering said magnetic field within said small area to be observed covering said points along said peripheral surface.

9. The probe as defined in claim 2, wherein said movable means are rotatable, said elongated member being of circular cross-section.

10. The probe as defined in claim 2, wherein said movable means comprise an outer ring gear and mounting means for rotatably mounting said probe to a fixed surface with said ring gear exposed on at least one side, said ring gear being sized such that when it is meshed with an adjacent similar such ring gear of an adjacent probe, said ring gear and said adjacent ring gear turn with a same rotational speed with an axis of rotation separated by a predetermined distance corresponding to a predetermined separation of adjacent interconnected rods of an interconnected rod assembly.

11. The eddy current probe as defined in claim 1, further comprising means for detecting and analyzing an impedance of said generating means as said generating means is moved along said elongated member and as said rotatable altering means is moved over said peripheral surface.

12. The probe as defined in claim 11, wherein said movable means comprise a ferromagnetic member for altering said magnetic field within aid small area to be observed covering said points along said peripheral surface.

13. The probe as defined in claim 7, further comprising means for detecting and analyzing an impedance of said generating means as said generating means is moved along said elongated member and as said rotatable altering means is moved over said peripheral surface, wherein said detecting and analyzing means comprise means for subtracting a signal from said pair of coils of said generating means from a signal from said coils of said correction probe.

14. The probe as defined in claim 1, wherein said generating means comprises: three said coils arranged to be spaced apart along said conductive elongated member; and two said movable means provided between said coils to provide said movable means on each side of a middle one of said coils, said movable means being positioned at different positions with respect to said peripheral surface.

15. The probe as defined in claim 14, further comprising means for detecting and analyzing an impedance of said generating means as said generating means is moved along said elongated member and as said rotatable altering means is moved over said peripheral surface, said detecting and analyzing means comprising a differential amplifier for producing a difference signal between outer ones of said three coils.

16. The probe as defined in claim 15, wherein said movable means comprise a pair of ferromagnetic members for altering said magnetic field, said ferromagnetic members being slightly offset from one another.

17. A method for non-destructive, eddy current testing of a conductive elongated member, comprising the steps of generating an oscillating magnetic field directed towards a cross-sectional peripheral surface of said member using a pair of coils arranged to be spaced apart along said member to produce an enhanced combined magnetic field component perpendicular to said surface in a space between said coils and a reduced magnetic field component along said member, altering said magnetic field within a small area to be observed substantially mid-way between said coils, moving said area alone said cross-sectional peripheral surface between said coils to cover points around said peripheral surface, and detecting and analyzing a permeability of said elongated member along said elongated member and at said points along said peripheral surface.

* * * * *